United States Patent
Bolmsjöet al.

(10) Patent No.: US 6,626,876 B1
(45) Date of Patent: Sep. 30, 2003

(54) METHOD AND APPARATUS FOR SELF-DRAINING OF URINE

(75) Inventors: Magnus Bolmsjö, Lund (SE); Sonny Schelin, Rockneby (SE)

(73) Assignee: ProstaLund Operations AB, Lund (SE)

( * ) Notice: Subject to any disclaimer, the term of this patent is extended or adjusted under 35 U.S.C. 154(b) by 114 days.

(21) Appl. No.: 09/704,223

(22) Filed: Nov. 1, 2000

(51) Int. Cl.[7] .................. A61M 1/00; A61M 25/00; A61B 5/04
(52) U.S. Cl. ............... 604/317; 600/574; 604/525
(58) Field of Search ............... 604/317, 323, 604/48, 329, 349, 544, 8, 105, 528, 523, 530; 606/204

(56) References Cited

U.S. PATENT DOCUMENTS

| | | | |
|---|---|---|---|
| 4,790,810 A | * | 12/1988 | Pugh, Jr. et al. |
| 5,176,664 A | * | 1/1993 | Weisman ............ 600/574 |
| 6,368,340 B2 | * | 4/2002 | Malecki et al. ........ 606/204 |

* cited by examiner

Primary Examiner—Michael J. Hayes
Assistant Examiner—Roz GhaFoorian
(74) Attorney, Agent, or Firm—John R. Ley

(57) ABSTRACT

A device for the drainage of the bladder through the body's own urethra opening outside of the human body, comprising a tube-shaped body (10). The tube-shaped body is comprised: to assume a first contracted position and for taken up within the bladder as well as a to assume a second partially extended position. At least one thread (14) extends between the bladder and an opening of the urethra and is attached at a first end of the tube-shaped body so that the tube-shaped body can be extended from the first position to the second position during the application of a pulling force upon the thread. The tube-shaped body in the second partially extended position extends in such a manner so as to exceed the distance between the bladder and the point of the urethra's closing. The tube-shaped body is comprised in such a manner that it will return to the first position upon the release of the pulling force on the thread.

The device is inserted into the bladder, in that a tube-shaped body is extended and inserted into an extended tube-shaped introducing member. The introducing member is inserted in through the urethra, so that the end piece of the tube-shaped body enters the bladder. The tube-shaped body is pushed out of the tube-shaped introducing member and into the bladder during the course of which it returns to the first contracted position completely within the bladder and in the course of which the placement of a thread that is attached to the tube-shaped body and that extends outside of the urethra is left to remain.

25 Claims, 4 Drawing Sheets

METHOD AND APPARATUS FOR SELF-DRAINING OF URINE

FIELD OF THE INVENTION

Prostate problems, such as benign prostate hyperplasia (BPH) or prostate cancer are usual occurrences among men. In many cases the symptoms experienced are very troublesome. Problems relating to the discharge of urine arise when the prostate gland swells to the extent that the urine duct, which runs through the prostate gland, is obstructed or pinched. The result of this process can lead to difficulties for the patient in being able to discharge urine at will, so-called urinary tract retention. Urinary tract retention can be either acute or chronic.

BACKGROUND OF THE INVENTION

The means for treating symptoms of urine retention is either surgery or another equivalent treatment, which removes the obstruction. Alternatively, the patient is required to have a catheter implanted or to learn so called self-draining. In the first case, a drainage catheter is placed into the urinary tract, from the penis and up into the bladder. The catheter is formed as a tube or a canal and is usually comprised of soft material, for example, latex, polyurethane, or silicone. At the end that lies in the bladder, the catheter is comprised of a balloon, which is blown up and prevents the catheter from slipping out. At the other end, outside of the penis, a clamp is usually attached so that the patient can open/close the catheter canal. Also urine can be collected by means of the attachment of a reservoir. The patient can also be taught to insert, on his own, a drainage catheter for him or herself into the bladder every time the urge to urinate arises and in that way can avoid the need to continually leave the catheter inside of him or herself.

There are a number of different forms of treatment with respect to obstruction by the prostate gland, such as surgery and treatment with heat. Aging problems in the form of acute urinary tract retention can arise, however, usually during a certain time after the treatment.

As relates to disease of the prostate, the type of assistance that is available today to many of those patients who have significant problems, and who no longer can rid themselves of urine spontaneously, is chronic catheter care in the form of continual use of a catheter. Alternatively, patients can be taught the technique of inserting an emptying catheter up through the urethra into the bladder every time the urge to urinate arises. However the patient must then always carry on his or her person sterile one-time use catheters. In certain more unusual cases, a stent can be placed into the prostate in order to stretch the tissue outward and allow the passage of urine. In the greatest majority of cases, however, a catheter is used. Disadvantages with all forms of catheter treatments, whether one uses an unremovable catheter or self-insertion, are that the patient's discomfort in using a catheter as well as the limitations on quality of life issues that come with it, i.e. socially, sexually, etc. In addition, there is a relatively high risk that urinary tract infections will arise through use of a catheter.

If the patient is determined to be an unsuitable subject to undergo a radical treatment of the disease by means such as surgery, due to weakness or other reasons use of a catheter will be required for the remainder of the patient's life.

Another usual form of treatment for obstructions caused by the enlargement of the prostate gland is by means of heat treatment using microwaves, radio waves, ultra sound or laser. The object of this type of treatment is to destroy a portion of the prostate tissue nearest to the urine through the urethra in order to achieve free passage of urine in this way. With such treatments, acute retention within the urinary tract usually arises. This is a result of the fact that the heat-treated prostate tissue becomes swollen. Thus, with respect to heat treatments, it is therefore quite usual that a catheter is inserted for approximately two weeks in order to insure the drainage of urine even during this period. Despite the fact that the drainage of urine is insured by using this method, the catheter in and of itself can result in problems for the patient.

SUMMARY OF THE INVENTION

One object of the above-named invention is to reduce the amount of displeasure experienced as a result of a patient's use of a catheter in association with the treatment of the prostate gland. Another object is to make possible the drainage of urine in association with other obstructions or another type of illness, for example, neurogenic bladder drainage disorders in women. This object can be attained through the characteristics set forth in patent claim 1.

According to the invention, a tube, a tube-shaped body, or a similar element that is coiled into one or more revolutions in the urine bladder is introduced. The bends in the tube make it so that it can not spontaneously slip out. The tube is relatively soft so that it can be stretched out if additional force is applied, and so that it will again assume its spiral shape if no outside force is applied.

All along the tube there are a number of small perforations into which the urine can run. In one end of the tube, a thread is attached. One free end of the thread runs out through the body's own urinary tract, which includes the urethra and penis/vagina. A small handle or stop can be made part of the thread in order to inhibit the end of the thread unintentionally receding into the urethra.

When the patient experiences the urge to urinate, or for any other reason desires to empty the bladder, the patient pulls on the thread. The end of the tube, which is attached to the thread is drawn down through the bladder, past the neck of the bladder and obstruction, and, in men, down through the prostate gland. The thread ought only be drawn to the extent that the end does not pass the apex of the prostate. Fittingly, a mark can be applied to the thread so that the treating doctor or nurse can designate how far the patient may draw so that the end will still remain inside of the prostate, yet will have passed the obstruction.

In such a manner, the patient can achieve drainage of the bladder. After drainage, the patient releases the thread, whereafter due to the spring mechanism that is a result of the tube's winding spiral shape, the end will again be drawn in so that the entire tube lies in the bladder. With the aid of the characteristics described in the invention, the tube is quite simple to apply, just as simple as inserting a normal drainage catheter.

As a result of the invention, a number of advantages are realized, among which are the following:

1. In the case that an obstruction that is hindering spontaneous emptying is of a temporary nature, for example after heat treatment, the patient himself will notice that he is again able to empty his bladder without means of assistance. He can then seek out medical assistance in order to remove the entire tube, or alternatively remove it himself.
2. The patient will experience a considerably lower degree of discomfort when he can avoid having a catheter inserted into the body or performing self-draining.

3. The risk of infection is likely to be considerably lower compared with catheter treatment.

DETAILED DESCRIPTION OF PREFERRED EMBODIMENTS

Figure 1:
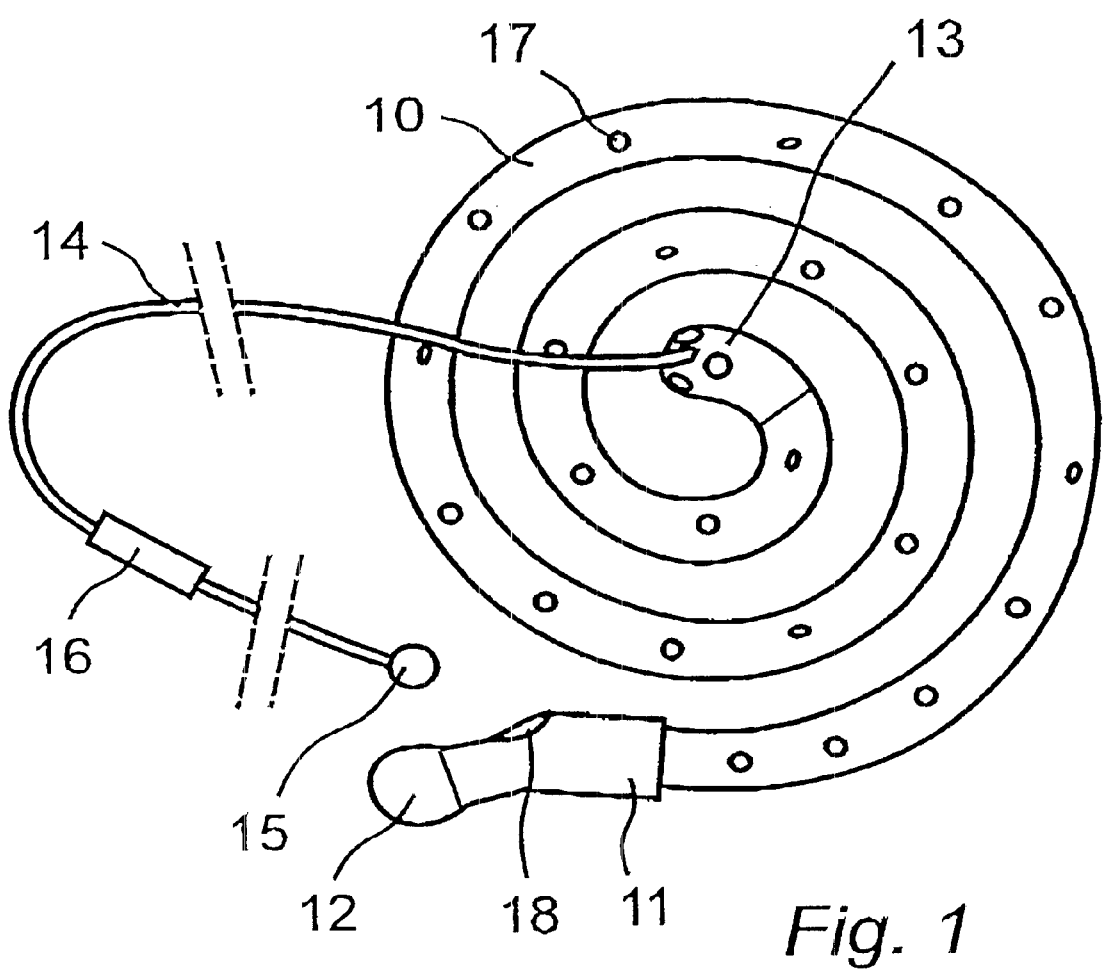
FIG. 1 shows an embodiment of a device in a receding state.

In the embodiment according to FIG. 1, a tube-shaped and extended body 10 has a first end that is attached with an end piece 11. The body 10 is formed as a flexible tube of polyurethane or similar material and assumes, in one embodiment shown in FIG. 1, the drawn together or rolled-up form. The end piece 11 is formed of a spherically formed ending 12, which makes possible the body's 10 introduction through the patient's urethra into the urine bladder. Through the application of a drawing pressure on the body 10, it can be caused to assume an extended form. A built in spring momentum, however, pulls the body 10 back to its contracted position when the pulling force is no longer applied.

A second end of the tube-shaped body 10 is formed of a special elastic or soft section 13. The soft section 13 is connected to a first end of a thread 14. The thread 14 is sufficiently long such that it, along with the entire tube-shaped body 10 introduced into the urine bladder, stretches itself out of the urinary canal of the patient. The urinary canal of a male patient is comprised of the urethra and the penis and for a female patient, the urethra and the vagina, more specifically, the entire distance from the urine bladder to the respective body opening.

At the thread's free end, there is a stop 15 in the form of a ball, or the like. After introduction of the body 10 into the urine bladder, the stop 15 prevents the thread from sliding into the urethra of the patient. A marker 16 on the thread makes it possible for the patient to control the drawing out of the thread 14 and body 10 to a suitable distance when used. The use is described in more detail below as referenced in FIGS. 6–8.

The entire body is provided with a plurality of holes 17 that allows for the urine to run into the body's hollow inner space The boles 17 are accordingly evenly distributed and are of such size that the risk of occlusion is small. A larger opening 18 is provided in the end piece 11 for the drainage of the urine bladder in association with the introduction of the body therein.

Figure 2:
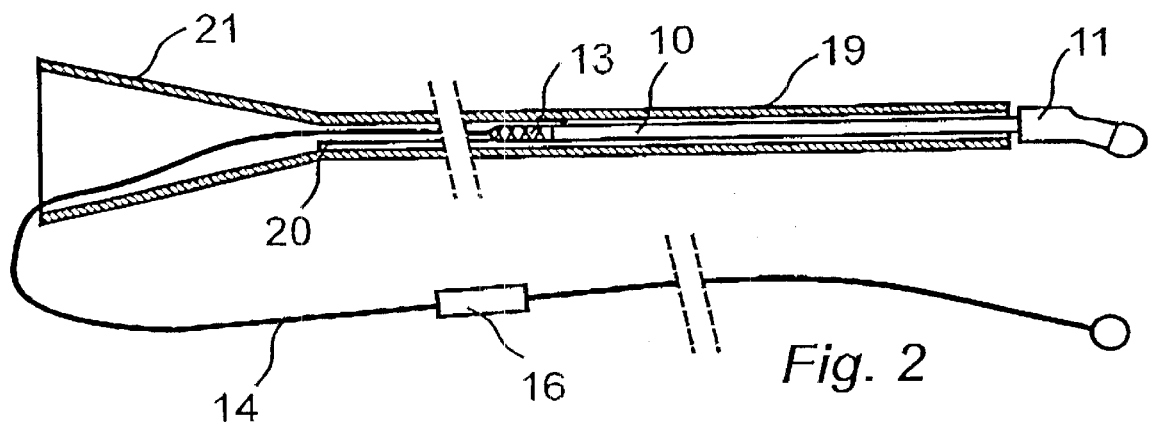
FIG. 2 shows the device in FIG. 1 in an extended state and introduced into an introducing member.

FIG. 2 depicts an introducing member 19. In the example provided, the introducing member 19 is comprised of a flexible tube that is open at both ends. Accordingly, the introducing member 19 is comprised of polyurethane or a similar material. One end of the introducing member 19 is comprised to have a conical part 21 for the purpose of making possible the introduction of a driving element (see description of FIG. 3). The conical part can also comprise a gripping means for the doctor or nurse who is using the device. In the center of the introducing member near the conical part, a guide thread 20 is attached. The guide thread 20 runs through the introducing member and makes it possible to eject the body 10 that has been placed within the introducing member 19.

In FIG. 2, the tube-shaped body 10 is introduced into the introducing member 19 and thereby extended to assume a second position. In its original state outside of the introducing member 19, the body 10, however, will attempt to reassume the shape as described in FIG. 1. The soft section 13 of the body 10 lies so that it is turned against the conical part 21 while the end piece 11 extends outside of the introducing member 19.

Figure 3:
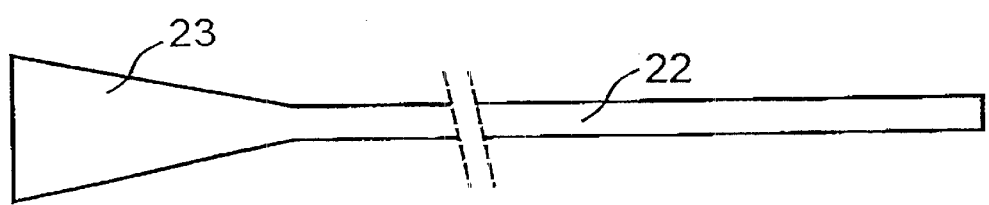
FIG. 3 shows a means that can be used to push the device in FIG. 1 out of the introducing member.

FIG. 3 displays an example of one embodiment of a driving element 22. Preferably the driving element 22 is comprised of a conical section 23 corresponding to the conical part 21 of the introducing member 19. Also in this embodiment the conical section 23 can be used as a gripping means.

Figures 4, 5:
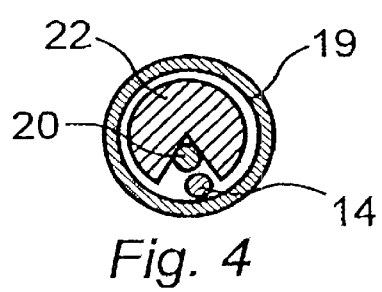
FIG. 4 is a cross-sectional view of the introducing member in FIG. 1 containing an already introduced first embodiment of a driving element.
FIG. 5 is a cross sectional view of the introducing member in FIG. 1 containing an already introduced second embodiment of a driving element.

FIG. 4 is a cross-sectional view, which shows the introducing member 19 wherein a first embodiment of the driving element 22 has been introduced. The driving element 22 has a circular cross-section with a receding slit for receiving a guide thread 20 and the thread 14. The driving element 22 is placed into the introducing member 19 when the introducing member is in the desired position with the end piece inserted into the bladder and with the driving element 22 pressing the tube-shaped body 10 into the urine bladder.

FIG. 5 is a cross sectional view, which shows the introducing member 19 along with an alternative embodiment of a driving element 22' introduced therein. The alternative driving element 22' is tube-shaped with a central inner cavity created for the purpose of drawing through it the thread 14. The guide thread 20 is not present in the embodiment exhibited according to FIG. 5.

Prior to insertion, the thread 14 is drawn through the introducing member 19 so that the thread extends outwardly into the rear conical part 21. Thereafter the user pulls on the thread 14 so that the whole body 10, with the exception of the end piece 11, is drawn into the introducing member 19. If a guide thread 20 is used, the body 10 will follow the guide thread 20 and its position will be stretched out accordingly. The end piece 11 is preferably formed with the same outer diameter as the introducing member 19. As a final aspect of the preparation for the introduction, the driving element 22, 22' is guided into the introducing member 19 from its end possessing the conical part 21 until the driving element 22, 22' lies against the soft section 13 of the body 10. The introduction of the driving element 22, 22' can also be postponed to a later time.

In the above-described embodiment, the entire device is inserted in its full length through the urethra and up into the bladder. The introducing member 19 should also be of such length so that the end piece is ensured of being introduced into the urine bladder. In a simple manner, the end piece's position can be monitored by the fact that urine drains from the introducing member 19. The driving element 22 can therewith be drawn out of the introducing member 19, or be provided with channels running along its surface for the purpose of drawing away urine when the driving element 22 is inserted into the introducing member 19.

After ensuring that the end piece is correctly positioned, the full-length of the driving element 22, 22' is inserted into the introducing member 19, wherewith the body 10 passes into the bladder and assumes its contracted form. Thereafter the driving element 22, 22' along with the introducing member 19 are drawn completely out of the urethra. During removal of the driving element 22, 22' and the introducing member 19, the thread 14 should not be placed under any pressure, but should slide out freely.

Figure 6:
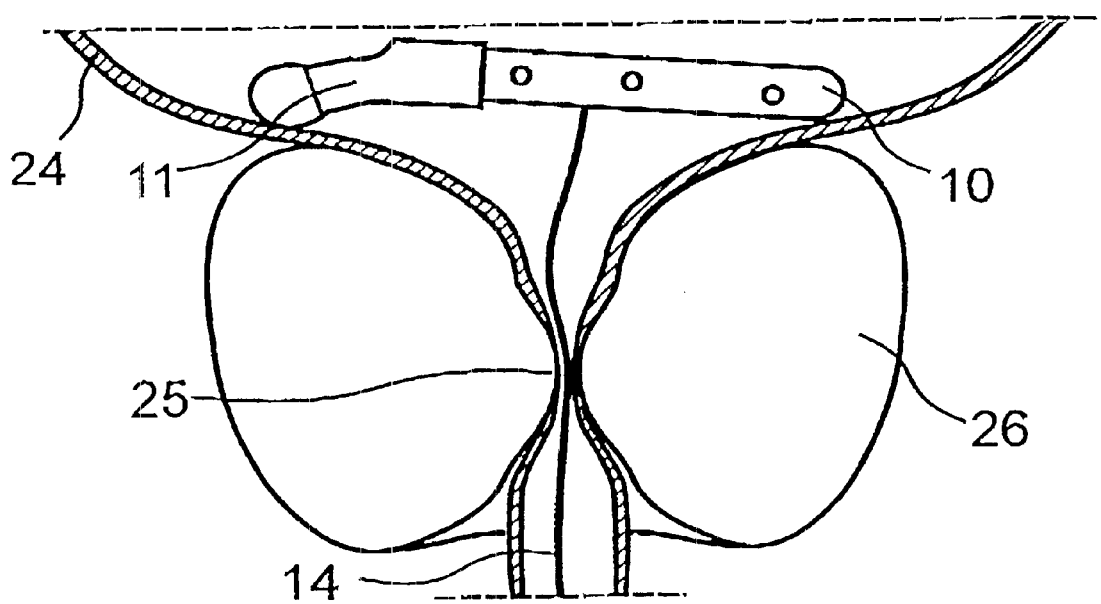
FIG. 6 shows a schematic view of the device in FIG. 1 fully introduced into a urine bladder.

FIG. 6 is a schematical view of the body 10 as introduced into the bladder 24 and with its end piece 11 resting against the urine bladder's wall. The thread 14 runs down through the point of the urethra's closing 25 and is accessible outside of the body. The point of the urethra's closing 25 is, as in the drawing provided, caused by the prostate tissue 26 that has been enlarged.

Figure 7:
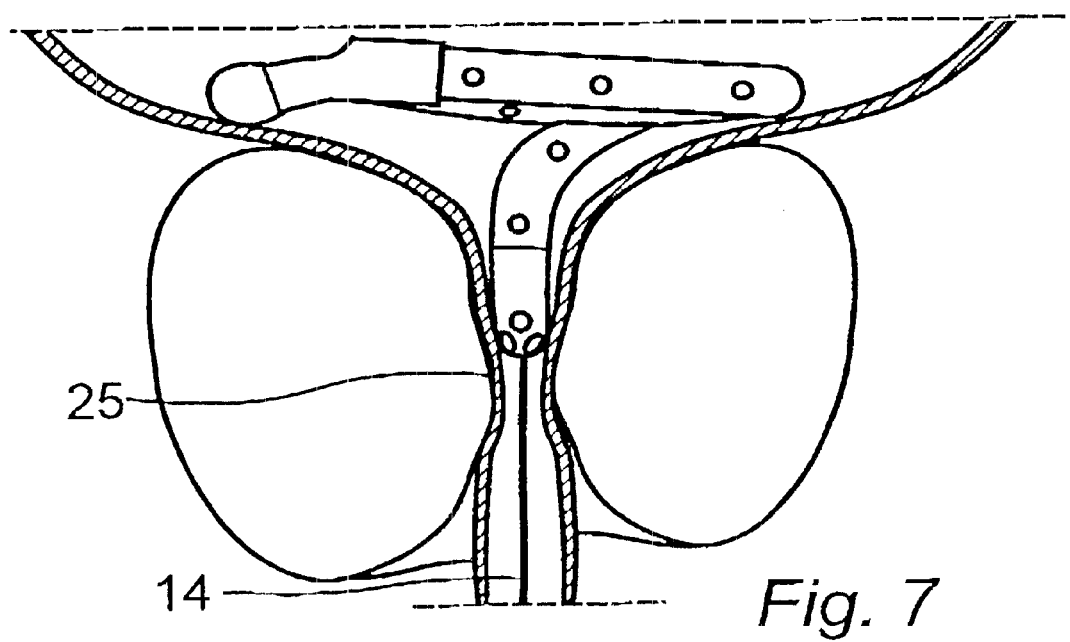
FIG. 7 shows the device in FIG. 6 extended to a first position partially drawn down into the urethra.
Figure 8:
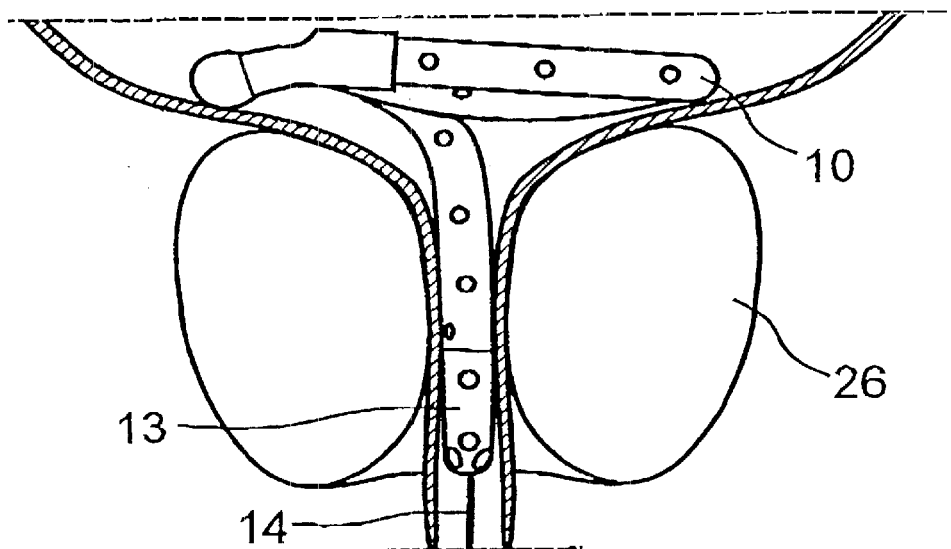
FIG. 8 shows the device in FIG. 6 extended to a second position drawn down into the urethra into such a position that the urine can freely flow out of the urine bladder.

When the urge to urinate arises or during other drainage of the bladder, the patient draws the thread 14, whereafter conditions in accordance with FIG. 7 will arise. The soft section 13 has been drawn down through the neck of the bladder and presses down upon tissue that is blocking the urethra when force is applied to the thread 14.

Additional drawing on the thread 14 results in the body 10 being drawn down through the prostate 26 and creates a canal, through which the patient can empty his bladder. These circumstances are exhibited in FIG. 8, where the soft section 13 has been completely drawn past the point of the urethra's closing 25. Urine can then freely pass through the tube-shaped body 10. After drainage has occurred the thread 14 is released wherewith the body 10 slowly returns to the contracted position shown in FIG. 1 and FIG. 6.

If the condition which has caused the point of the urethra's closing 25 abates, for example after a certain time subsequent to heat treatment of the prostate, the entire device can be removed by the patient simply drawing out the entire thread 14. The body 10 will then follow in the same path of removal without damaging the urethra or other tissue.

In addition to polyurethane other similar pliable materials can be used to form the tube-shaped body 10, the introducing member 19, and the driving element 22, 22'. An example of such material is silicone. The introducing member 19, however, should have a certain rigidity so that the tube-shaped body can be safely pushed through it.

Figure 9:
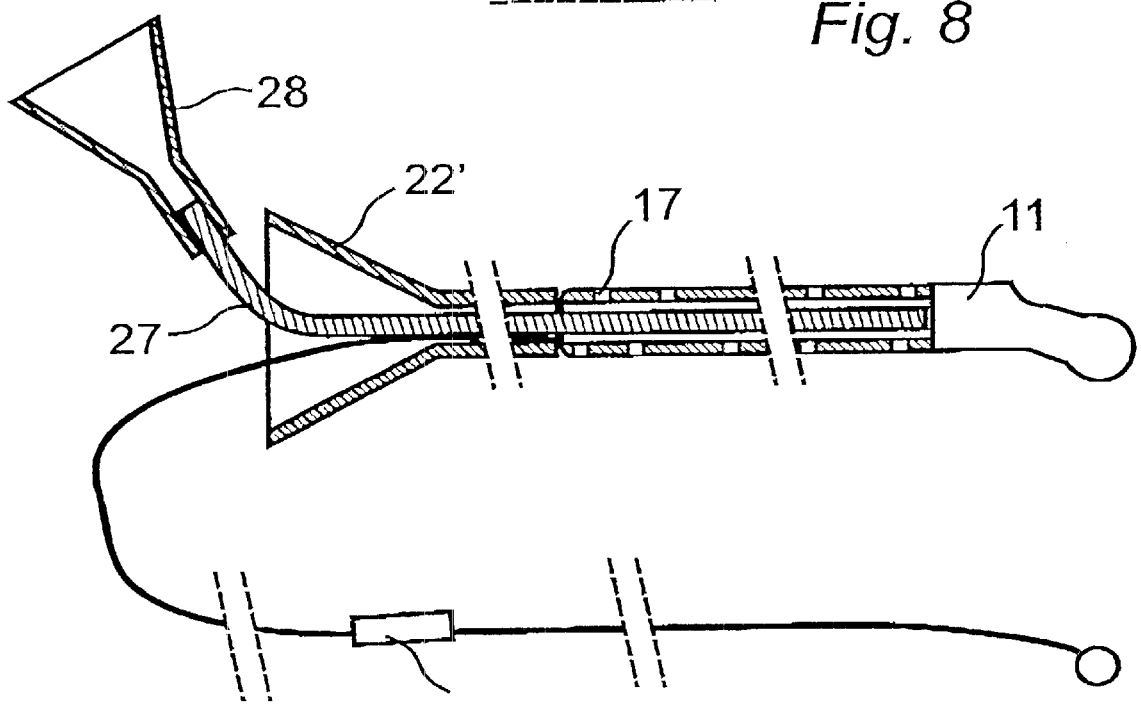
FIG. 9 shows a schematic view drawing of an alternative embodiment of an introducing member.

In the embodiment according to FIG. 9, the introducing member is comprised so that a flexible guide thread 27 has an outer dimension less than the diameter of the tube-shaped body's 10 inner diameter. In order to facilitate the use of the introducing member, the thread 27 is provided with a gripping means 28. In the exhibited embodiment, a circular cross-section is used. The driving element 22' also in this embodiment is tube-shaped.

In the embodiment exhibited in FIG. 9 the driving element 22', like the entirety of the tube-shaped body 10, is guided via the flexible guide thread 27. Accordingly, the flexible guide thread 27 is extended throughout essentially the entirety of the tube-shaped body 10. One advantage of this embodiment is that the tube-shaped body 10 can be created to possess a greater outer diameter and therewith offer enhanced drainage capacities. The flexible guide thread 27 can be comprised of a spun or wound piano wire or a similar material and should be sufficiently rigid so that the tube-shaped body 10 remains in the second extended position when it is moved over the guide thread 27.

What is claimed is:

1. Apparatus for draining urine from a bladder through a bladder neck and into a urethra and past an obstruction to the urethra and through a urinary canal to an exterior opening of the urinary canal in a human being, comprising:

an elongated body which normally forms into a curved shape having a spring-like characteristic which permits the body to be temporarily straightened under external force, the body defining an inner space which extends along the elongated body between a first end and a second end, the body also defining at least one opening from an exterior of the body into the inner space;

a first end piece connected at the first end of the body across the inner space of the body, the first end piece having a curved exterior end configuration to facilitate insertion of the straightened body from the exterior opening of the urinary canal and through the urethra and bladder neck and into the bladder;

the spring-like characteristic of the body re-forming the body from a straightened configuration into the normal curved shape in the bladder after insertion of the body into the bladder;

the spring like characteristic and the normal curved shape of the body restricting unintentional movement of the body through the bladder neck and into the urinary canal;

a second end piece connected at the second end of the body across the inner space of the body, the second end piece having a pliability characteristic to facilitate movement of the second end piece from within the bladder through the bladder neck and into the urethra and to straighten the second end of the body upon movement of the second end of the body through the bladder neck and into the urethra; and a thread having a sufficient length to extend from the second end piece through the urinary canal when the body is in the normally curved shape in the bladder, the thread connected at one end to the second end piece to direct the second end piece from the bladder through the bladder neck and into the urethra and to straighten and move the second end of the body from the bladder into the bladder neck and urethra in response to a pulling force applied to the other end of the thread at a location exterior of the exterior opening of the urinary canal;

the pulling force moving the second end piece and the second end of the body past the obstruction in the urethra to establish a flow path for urine from the bladder through the inner space and into the urethra and the urinary canal; and the spring-like characteristic of the body withdrawing the second end of the body and the second end piece from the urethra and past the bladder neck and re-forming the normal curved shape of the body in the bladder upon releasing the pulling force on the thread.

2. An introducing member for inserting the urine draining apparatus defined in claim 1 into the bladder, wherein:

the introducing member has a length sufficient to extend from the exterior opening of the urinary canal through the urinary canal;

the introducing member has a transverse dimension to fit within the urinary canal from the exterior opening of the urinary canal to the bladder neck; and the introducing member defines a cavity extending entirely along the length of the introducing member, the cavity having transverse dimension to receive the body of the urine draining apparatus therein when the body is temporally straightened.

3. An introducing member for inserting the urine draining apparatus defined in claim 1 into the bladder, wherein:

the introducing member is elongated has a length sufficient to extend from the exterior opening of the urinary canal through the urinary canal;

the introducing member comprises a flexible guide having an external dimension to fit within the inner space of the body; and the flexible guide has sufficient rigidity to temporarily straighten the body upon positioning the flexible guide within the inner space of the body and to insert the body and the flexible guide while within the inner space from the exterior opening of the urinary canal through the urinary canal and to introduce the urine draining apparatus into the bladder.

4. Apparatus as defined in claim 1, wherein:

a marker attached to the thread at a predetermined location between the ends of the thread to indicate the extent to which the pulling force should move the thread out of the urinary canal relative to the exterior opening of the urinary canal to pass urine from the bladder through the inner space and into the urinary canal.

5. Apparatus as defined in claim 4, wherein:

the predetermined location of the marker causing the marker to withdraw into the urinary canal upon the body reforming into the normal curved shape within the bladder.

6. Apparatus as defined in claim 1, wherein:

the pliability characteristic of the second end piece defines a relatively greater elasticity compared to the body to facilitate movement of the second end piece into the bladder neck.

7. Apparatus as defined in claim 6, wherein:

the second end piece includes a curved end configuration.

8. Apparatus as defined in claim 7, wherein:

the second end piece includes at least one opening extending from the inner space through the second end piece to pass urine from the inner space through the second end piece into the urinary canal.

9. Apparatus as defined in claim 1, wherein:

the second end piece includes a curved end configuration to facilitate movement of the second end piece from within the bladder through the bladder neck.

10. Apparatus as defined in claim 9, wherein:

the curved end configuration of the second end piece is rounded.

11. Apparatus as defined in claim 10, wherein:

the second end piece includes at least one opening extending from the inner space through the second end piece to pass urine from the inner space through the second end piece into the urinary canal.

12. Apparatus as defined in claim 9, wherein:

the second end piece includes at least one opening extending from the inner space through the second end piece to pass urine from the inner space through the second end piece into the urinary canal.

13. Apparatus as defined in claim 1, wherein:

the first end piece defines a through opening extending from the exterior of the first end piece through the first end piece and into the inner space to pass urine from the bladder into the inner space.

14. Apparatus as defined in claim 13, wherein:

the through opening extends through the curved exterior end configuration.

15. Apparatus as defined in claim 13, wherein:

the curved exterior end configuration of the first end piece includes a generally spherically shaped portion.

16. Apparatus as defined in claim 1, wherein:

the first end piece has a maximum transverse dimension greater than a maximum transverse dimension of the body.

17. Apparatus as defined in claim 16, wherein the first end piece and the body each have a generally circular transverse cross-sectional configuration; and the maximum cross-sectional diameter of the first end piece is greater than the maximum diameter of the body.

18. Apparatus as defined in claim 1, wherein:

the body comprises a tube defining the inner space.

19. Apparatus as defined in claim 18, wherein:

the body defines a plurality of openings formed through the tube to the inner space at a plurality of spaced apart locations along the length of the body to pass urine between the exterior of the body and the inner space.

20. Apparatus as defined in claim 1, wherein:

the body defines a plurality of openings extending from the exterior of the body to the inner space to pass urine between the exterior of the body and the inner space.

21. Apparatus as defined in claim 1, wherein:

the body comprises flexible material which inherently creates the spring-like characteristic.

22. Apparatus as defined in claim 1, wherein:

the thread has sufficient length to extend the other end of the thread beyond the exterior opening of the urinary canal, and further comprising:

a stop attached to the other end of the thread at a position which remains outside of the exterior opening of the urinary canal when the body re-forms into the normal curved shape, the stop preventing the other end of the thread from sliding into the urinary canal.

23. Apparatus as defined in claim 1, wherein:

the thread has sufficient length to extend the other end of the thread beyond the exterior opening of the urinary canal, and further comprising:

a handle attached to the other end of the thread at the position which remains outside of the exterior opening of the urinary canal when the body re-forms into the normal curved shape, the handle facilitating gripping the other end of the thread to apply the pulling force to the thread.

24. Apparatus as defined in claim 1, wherein:

the normal curved shape of the elongated body is coiled.

25. Apparatus as defined in claim 24, wherein:

the normal curved shape of the elongated body is coiled in a spiral; and the spring-like characteristic of the body positions the second end piece generally within an interior coil of the spiral when the body re-forms into the normal curved shape within the bladder.

* * * * *